(12) United States Patent
DiFonzo et al.

(10) Patent No.: US 10,605,774 B2
(45) Date of Patent: Mar. 31, 2020

(54) MAGNETIC IMAGING

(71) Applicant: Apple Inc., Cupertino, CA (US)

(72) Inventors: John C. DiFonzo, Emerald Hills, CA (US); Jean-Marc Gery, Los Angeles, CA (US)

(73) Assignee: APPLE INC., Cupertino, CA (US)

( * ) Notice: Subject to any disclaimer, the term of this patent is extended or adjusted under 35 U.S.C. 154(b) by 586 days.

(21) Appl. No.: 14/857,534

(22) Filed: Sep. 17, 2015

(65) Prior Publication Data
US 2017/0082580 A1 Mar. 23, 2017

(51) Int. Cl.
*G01N 27/72* (2006.01)

(52) U.S. Cl.
CPC ............... *G01N 27/72* (2013.01)

(58) Field of Classification Search
CPC ................................................ G01N 27/72
USPC .. 324/234, 200, 207.13–247, 259, 262, 529, 324/750.21, 53, 754.17, 500, 754.29, 324/117 R
See application file for complete search history.

(56) References Cited

U.S. PATENT DOCUMENTS

| | | | |
|---|---|---|---|
| 5,364,689 A | 11/1994 | Kashiwagi et al. | |
| 5,411,398 A | 5/1995 | Nakanishi et al. | |
| 6,720,766 B2 * | 4/2004 | Parker | A61B 8/587 324/308 |
| 8,523,236 B2 | 9/2013 | Leary | |
| 9,224,529 B2 | 12/2015 | Gery | |
| 2003/0013280 A1 * | 1/2003 | Yamanaka | C23C 16/24 438/487 |
| 2006/0150854 A1 | 7/2006 | Benninger et al. | |
| 2008/0030290 A1 * | 2/2008 | Norman | B43L 1/004 335/296 |
| 2008/0218299 A1 * | 9/2008 | Arnold | B81C 1/00007 335/306 |
| 2014/0029823 A1 * | 1/2014 | Birkbeck | G06T 7/0081 382/131 |
| 2016/0093424 A1 | 3/2016 | Zhu et al. | |

* cited by examiner

*Primary Examiner* — Melissa J Koval
*Assistant Examiner* — Trung Nguyen
(74) *Attorney, Agent, or Firm* — Dorsey & Whitney LLP (57) ABSTRACT

A magnetic image system for providing a visible image includes a magnetic substrate having a first and a second opposing surface and formed of material that is magnetized into a pattern of magnetized regions corresponding to the visible image, the magnetized regions forming a magnetic surface having a size and a shape in accordance with the visible image and a magnetic property corresponding to a visible image property, wherein the magnetic surface is rendered visible as the visible image using a magnetic imaging medium that interacts with the magnetic surface in accordance with the magnetic property.

20 Claims, 10 Drawing Sheets

MAGNETIC IMAGING

FIELD

The described embodiments relate generally to the magnetization of permanent conductive substrates, and more specifically to methods and systems for selectively forming magnetized regions that can be used as a magnetic imaging mask used as part of a magnetic imaging system.

BACKGROUND

Multi-pole magnetic substrates made from magnetic materials such as rare earth elements have found application in the industrial arts, especially for uses relating to the enclosures and casings for personal computerized products such as laptops, tablets and smart phones.

Other uses of multi-pole magnetic substrates are also possible.

SUMMARY

A method for forming a magnetic image is described. The method is a carried out by using a magnetic imaging mask having a masking element to generate at a magnetic substrate magnetized regions each having a magnetic property and arranged in pattern that corresponds to the magnetic image. A magnetic imaging medium magnetically interacts with the magnetized regions in accordance with the magnetic property.

An electronic device includes a housing having a magnetic surface at an exterior surface of the housing, the magnetic surface corresponds to a magnetic image and has a magnetic property corresponding to a visible image property. The electronic device can also have the magnetic surface as a separate piece joined or associated with the housing if the housing is not magnetic.

A magnetic image system includes a magnetizer arranged to provide a magnetic field, a magnetic mask having masking elements arranged in a pattern corresponding to a magnetic image, the masking elements are associated with a shielding factor corresponding to an image property. A magnetic substrate is positioned relative to the magnetizer and the magnetic mask such that the magnetic mask shields a corresponding portion of the magnetic substrate from the magnetic field in accordance with the shielding factor resulting in a magnetized region providing a magnetic surface having a magnetic property corresponding to the image property.

This Summary is provided merely for purposes of summarizing some example embodiments so as to provide a basic understanding of some aspects of the subject matter described herein. Accordingly, it will be appreciated that the above-described features are merely examples and should not be construed to narrow the scope or spirit of the subject matter described herein in any way. Other features, aspects, and advantages of the subject matter described will become apparent from the following Detailed Description, Figures, and Claims.

Other aspects and advantages of the embodiments described herein would become apparent from the following detailed description taken in conjunction with the accompanying drawings which illustrate, by way of example, the principles of the described embodiments.

BRIEF DESCRIPTION OF THE DRAWINGS

The described embodiments may be better understood by reference to the following description and the accompanying drawings. Additionally, advantages of the described embodiments may be better understood by reference to the following description and accompanying drawings in which.

DETAILED DESCRIPTION

In the following detailed description, references are made to the accompanying drawings, which form a part of the description and in which are shown, by way of illustration, specific embodiments in accordance with the described embodiments. Although these embodiments are described in sufficient detail to enable one skilled in the art to practice the described embodiments, it is understood that these examples are not limiting; such that other embodiments may be used, and changes may be made without departing from the spirit and scope of the described embodiments.

The foregoing description, for purposes of explanation, uses specific nomenclature to provide a thorough understanding of the described embodiments. However, it will be apparent to one skilled in the art that the specific details are not required in order to practice the described embodiments. Thus, the foregoing descriptions of specific embodiments are presented for purposes of illustration and description. They are not intended to be exhaustive or to limit the described embodiments to the precise forms disclosed. It will be apparent to one of ordinary skill in the art that many modifications and variations are possible in view of the above teachings.

The described embodiments relate to a system and method for forming discrete magnetic regions at a magnetic substrate that can be used to form a magnetic image. The magnetic image in and of itself is not generally visible but can, nonetheless, be rendered visible using a magnetic imaging medium that magnetically interacts with the magnetic regions. An image property, such a luminance, can be related to a nature of the magnetic interaction between the magnetic regions and the magnetic imaging medium and can also be related to a level of magnetization of the magnetic regions. For example, a level of magnetization can range in a stepwise fashion (or in a continuous fashion) between essentially no magnetization to a saturation of the magnetic substrate. In other words, a degree of interaction between the magnetic imaging medium can be related to the level of magnetization that can, in turn, affect aspects of the visible image.

More specifically, the described embodiments are related to a capability of creating a magnetic image based upon a two-dimensional array of magnetized regions. In addition to being magnetized simply as North or South, the magnetic regions can be magnetized to include intermediate magnetization levels that can range from essentially no magnetization to a level corresponding to a full magnetic saturation of the magnetic substrate. The magnetic regions can, in turn, magnetically interact with a magnetic imaging medium and be rendered visible as a gray-scale image. As is well known, gray-scale is a range of monochromatic shades from black to white and therefore contains only shades of gray and no color. Each picture element (or pixel) used to form a gray-scale image has a luminance value related to a degree of magnetic interaction between the magnetized regions and the magnetic imaging medium, which can be in accordance with a scale from dark to light. For example, a conventional eight (8) bit digital imaging system can support $2^8$, or 256 levels of luminance per pixel where "0" and "255" represent the range of luminance values available. Therefore, by analogy, a level of magnetization up to and including saturation of the substrate can correspond to a magnetic "luminance" indicating a degree of magnetic interaction with the magnetic imaging medium. In this way, a region (or pixel) having a higher level of magnetization will have a potentially greater magnetic interaction with the magnetic imaging medium. Other optical characteristics besides luminance can be used to render the magnetic image visible. For example, an imaging plate using the Kerr effect (mentioned elsewhere) will have its polarization changed by the magnetic pixels that can result in a color change.

For example, if the magnetic region has a low level of magnetization, then the capability of the magnetic region to magnetically interact with the magnetic imaging medium will also likely be low. In this case, visual rendering of the magnetic image will likely result in the magnetic substrate associated with the magnetic region being visible, or at least contributing a substantial proportion of the visible image corresponding to the magnetic region. Accordingly, a degree of magnetic interaction between the magnetized region and the magnetic imaging medium can be correlated to a magnetic luminance value that can be considered a magnetic analog to an optical luminance value. It should be noted that while it is not possible with conventional digital imaging system to extend the luminance range beyond the number of levels associated with the resolution of the system, a magnetically based imaging system, however, can take advantage of the fact that the magnetic regions have two possible polarization states, $P_1$ or $P_2$ (or in conventional terms, North or South). Accordingly, an eight bit magnetically based imaging system can support $2 \times 2^8$ or 512 levels of luminance per pixel since each pixel can be associated with a luminance level for each polarity.

Analogous to conventional photography, a version of the magnetic image can be created by magnetizing a substrate using an external magnetic field attenuated by a magnetic mask having electrically conductive elements patterned in accordance with the magnetic image. It should be noted that a picture element (hereinafter referred to as a magnetic pixel) can be represented as a discrete magnetic region having an associated magnetic imaging property based upon a level of magnetization and polarity. For example, a magnetic region that is not magnetized can be associated with a magnetic pixel having a "luminance" value of "0" indicating zero or no magnetic field and therefore little or no interaction with a magnetic imaging medium. On the other hand, a magnetic pixel having a greater level of magnetization can be associated with a magnetic pixel having a luminance value of "B" where B is the "bit depth" of the system (for example, as above, an 8-bit system will have 255 luminance levels each associated with a different magnetization level for a given magnetic pixel). It should be noted that since any magnetic region can be magnetized to have one of two magnetic polarities, the actual dynamic range of the magnetic imaging system is actually twice as large as a conventional digital optical imaging system. For example, a particular magnetic pixel can have a luminance value based upon a level of magnetization independent of the magnetic polarity.

The resolution of the magnetic image can be associated with a number of magnetic regions in a given area and a distance between each. In this regard, controlling a transition zone between each magnetic region is important as the wider the transition zone, the fewer and less dense the magnetic image. In other words, the ultimate resolution of the magnetic image can be bounded by an ability to form distinct magnetic regions with a specified area that can depend upon the ability to create well-defined transition zones between magnetic regions. For example, forming a magnetic region associated with a magnetic pixel can be accomplished using a magnetic masking technique shown an described in co-pending U.S. Patent Application entitled: "Multi-pole Magnetization of a Magnet" by Gery et. al. having patent Ser. No. 14/148,563 filed Jan. 6, 2014 that is incorporated by reference in its entirety for all purposes.

In one approach, the conductivity of selected magnetic masking elements can be altered in such a way as to affect the formation of eddy currents in that magnetic masking element that, in turn, affects the ability of a magnetic field to alter the magnetic properties of the underlying magnetic substrate. For example, assuming that a magnetic mask is formed of a conductive material such as copper, by varying the conductivity of the copper (by alloying copper, thinning, etc.) in a range from low conductance to high conductance in discreet steps, a number of discreet magnetic levels can be created in underlying magnetic substrate associated with each step of conductivity in the copper magnetic mask. It should be noted that more or fewer magnetic levels can be produced depending on the size of the magnetic pixels, the grade and thickness of the magnetic substrate, and the magnetic scanning method. It should also be noted that there are two kinds of saturation in hard magnetic materials: 1) saturation of virgin material to assure that all of the magnetic domains have been magnetized. This magnetization is done is two steps with masks that mask opposite regions of the material, and magnetize the substrate in opposite polarities. This is a two-step process, but has the advantage that virgin material requires a lower energy pulse to be fully saturated (since there is not any magnetization that's already imposed on the material that has to be counteracted). This is actually a big advantage when working with high coercivity grades of rare earth magnets and can enable the use of significantly smaller and cheaper magnetizer circuits; and 2) saturation of domains to align them all in a particular polarization. In the context of this discussion, it is assumed that that any hard magnetic part will have been previously saturated to satisfy in order to satisfy condition (1).

It should be further noted that there are many ways to alter the opacity to magnetic flux of a magnetic masking element. For example, the conductivity of the mask material can be altered rendering the mask material more or less able to support eddy currents. Moreover, the thickness of the mask material can be varied, the mask shape can be changed from, for example, a uniform area to a "labyrinth" or "maze" of mask material changing multiple times within the mask, resulting in an average density lower than that of a uniform mask. This approach, in particular, can be especially advantageous if the mask is configured as a multi-layer PCB, in which the conductive traces are the mask material, thus allowing fine control of the mask pattern using printed circuit boards and the manufacturing advantages of this mature technology. Furthermore, the substrate can be magnetized in multiple steps by fixtures having different patterns and opacities, or any combination of the ways listed above.

Once a version of the magnetic image has been formed on the magnetic substrate using the magnetic mask, there are multiple ways to scan or view (or "develop) the magnetic image using magnetic imaging medium that can interact with magnetic regions formed in the magnetic substrate. For example, iron filings placed on the magnetic substrate will arrange themselves along magnetic field lines. In another possible implementation, screens that use iron filings encapsulated into plastic laminations are readily available and can be used to view magnetic images. "Magnetic" paper can also be use to view the magnetic image as well as certain materials that react a magnetic field with visible light.

A magnetic image can be useful for several purposes: a magnetic film (such as used in recording tape and credit cards) can be applied to the back of an enclosure, a unique and identifying image can be imprinted on the enclosure from the outside. This image will be invisible unless scanned by a suitable method. The image can then be used as a steganographic security feature. By varying the pattern, or applying the pattern in multiple steps with varying imaging fixtures, the pattern can be unique to the particular unit on which it is imprinted. The image can be a novelty decoration that appears only when two parts of a device (one magnetized in a pattern, a second part have a magnetically sensitive area) are brought together. The image can be used to hold coded information meant to be read by another device. In this case it will act like a QR code, bar code, or magnetic ink identification number. However, because it is not limited to a binary pattern (N/S, or black/white) it can hold the information in a denser method (base 4 or 8, for example) and so be much smaller or hold more information in the same space. The enclosure or device can be fabricated from a soft magnetic material that is designed to have a certain amount of coercivity (such as soft, low carbon steel, or 400 series stainless steel). The surface of the device can then itself be magnetically imprinted for the purposes listed above. Note also that while this disclosure emphasizes 2D gray scale patterns, 1D patterns are also possible and may be useful. Moreover, imaging a magnetic pattern on a magnetic substrate such as iron can be used as a magnetic detector by observing a pattern developed in the magnetic substrate caused by the external magnetic field. In this way, a quantitative idea of what iron was subjected to (symmetry, field strength, etc,) be available.

It should be noted that unlike other image coding methods, a magnetic image includes both positive and negative values. This can be used to print two different images on the same substrate, one in the positive range and the other in the negative. Then imaging material sensitive to one or the other polarity can be applied to it to produce one or the other image. Moreover, it is also possible to make a substrate having two or more different magnetic materials with different values of coercivity (or alternatively layers of thin substrates). One can then imprint multiple images on the substrate by first applying a field strong enough to magnetize the highest coercivity material; following that, one imprints a second image at a lower field strength that can magnetize a second material with lower coercivity but not the first; and so on until all the various materials are magnetized.

Illustrated in FIGS. 1-9 are several representative embodiments of a system and method for forming a magnetic imaging that can include a magnetic imaging mask that can be used to form the magnetic image. The recited advantages are not meant to be limiting in any way, however, as one skilled in the art will appreciate other advantages may also be realized upon practicing the present disclosure. In addition, it is also to be appreciated that the various aspects, embodiments, implementations or features of the described embodiments can be used separately or in any combination, and that other uses and applications are also possible and may be considered to fall within the scope of the present disclosure.

As used herein, the term "permanent magnet" refers to a magnet that is magnetized and maintains its own persistent magnetic field after removal from a magnetizer. The strength and polarity of the magnet's persistent magnetic field is changeable; however, a change in polarity involves exposure of the magnet to an external magnetic field having sufficient strength to re-align the magnetic domains in the magnetic material. In other words, an amount of energy must be provided by a magnetizing magnetic field to change a magnetic domain from a first polarity to a second polarity (such as N to S or vice versa).

Figure 1A:
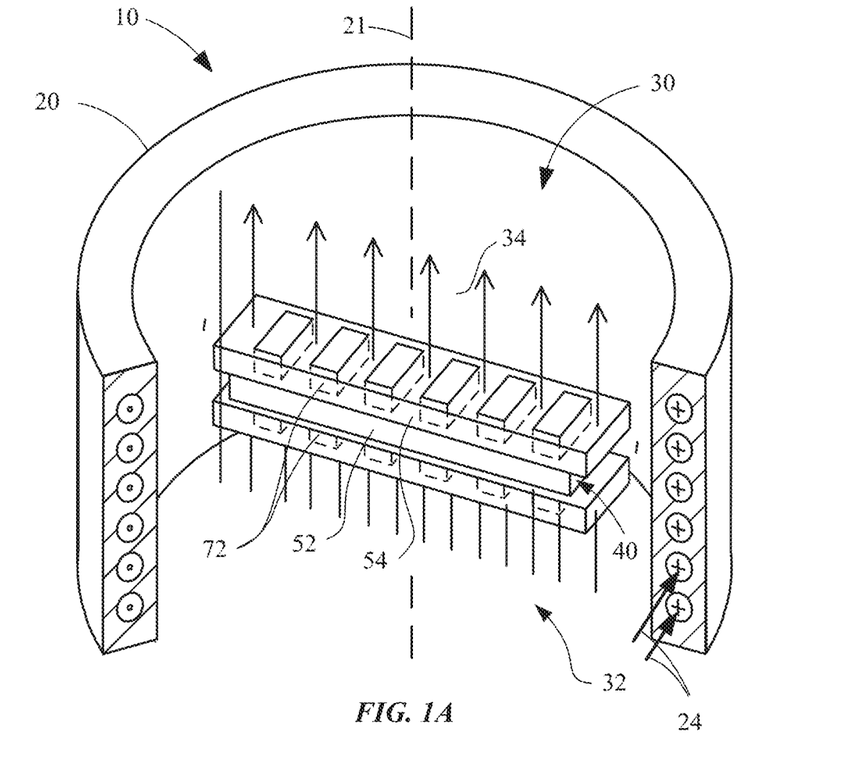
FIGS. 1A-1C are perspective, cut-away views of a permanent magnet disposed within the magnetizing zone of a magnetization system, in accordance with one representative embodiment of the present disclosure.
Figure 1B:
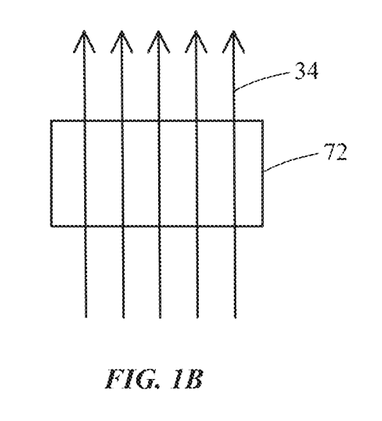
Figure 1C:
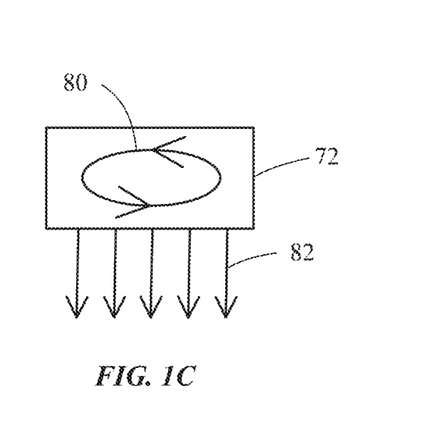

Referring now in more detail to the figures, wherein like parts are identified with like reference numerals throughout the several views, FIG. 1A is a perspective, cutaway view of a magnetization system 10 for creating a version of a magnetic image in a magnetic substrate using a magnetic imager in the form of a magnetic mask, in accordance with one embodiment of the present disclosure. The magnetization system 10 generally includes a magnetization coil 20 made of windings 24 formed of conductive material. Magnetization coil 20 is depicted as being centered about a central axis 21. The internal volume defined by the magnetization coil 20 can be considered a magnetization zone 30. The magnetization coil 20 further includes a power or current source (not shown, but known to one of skill in the art) that is configured to direct an electric current through the windings 24 in the magnetization coil 20 so as to generate a magnetic field 32 within the magnetization zone 30. As shown in FIG. 1B, when current is directed through windings 24 of the magnetization coil 20 in a first direction, a polarity of the magnetic field 32 is positive with flux lines 34 directed upwards and substantially parallel to the central axis 21 of the magnetization coil 20.

A magnetic substrate 40 made from a magnetic material, including but not limited to rare earth metal alloys such as Neodymium Iron Boron (NdFeB) or Samarium Cobalt (SmCo), is positioned within the magnetizing zone 30 of the magnetization coil 20. The magnetic substrate 40 is generally positioned in an orientation that is transverse to the central axis 21 of the magnetization coil 20, so that the flux lines 34 of the magnetic field 32 are perpendicular (or thereabouts) and extend through the thickness of the magnetic substrate 40. However, in other aspects the magnetic substrate 40 may be positioned in any orientation relative to the central axis 21 of the magnetization coil 20.

Also shown in FIG. 1A is a magnetic mask that includes shield bodies 72 that are patterned that correlates to the magnetic image. The shield bodies 72 can be used to subdivide the magnetic substrate 40 into masked regions 52 and exposed regions 54, with both sides of the masked regions 52 of the magnetic substrate 40 being covered by shield bodies 72. The shield bodies 72 are generally formed from a highly-conductive material such as copper or silver, and are provided with a length, width and thickness that allows for the formation of eddy currents 80 within the shield bodies 72 in response to the magnetic field or flux lines 34 (FIG. 1B) passing through the shield bodies 72. In turn, the eddy currents 80 generate a counter magnetic flux 82 (FIG. 1C) that opposes the flux lines 34 generated by the magnetization coil 20, thereby shielding the masked regions 52 of the magnetic substrate 40 from the magnetic field (FIG. 1A). As a result, only the magnetic domains located within the exposed regions 54 of the magnetic substrate 40 will be magnetized or re-magnetized with the same polarity as the magnetic field and at a level of magnetization in accordance with coercivity of magnetic substrate 40. It should be noted, however, that by varying the relevant properties of shield bodies 72, formation of eddy currents could be enhanced or reduced in accordance with a desired magnetic property of the masked regions 52 that can be used to alter properties of the corresponding magnetized region.

When the magnetization coil 20 is activated or energized by directing a current 26 through the windings 24 that form the coil 22, the shield bodies 72 can function as a stencil that alternately shields the masked regions 52 of the magnetic substrate 40, while exposing the unprotected regions 54 to the full effects of the flux lines 34 of the magnetic field 32. As described above, the shielding effects of the shield bodies 72 can be achieved through the induced formation of eddy currents 80 within the shield bodies 72 induced by the applied flux lines 34.

As understood by one of skill in the art, the rare earth magnetic materials that form the magnetic substrate 40 generally have a high coercivity (i.e. resistance to withstand an externally magnetic field) before the magnetic domains in the material changes to a new alignment. In other words, the field strength of the externally magnetic field passing through the magnetic material must exceed an energy threshold before the magnetic domains begin to become aligned with the flux lines 34 of the magnetic field. The counter magnetic flux 82 (FIG. 1C) generated by the eddy currents 80 can oppose or deflect the flux lines 34 of the magnetic field to a degree that reduces the magnetic field below the energy threshold in the masked regions 52 of the magnetic substrate 40. As a result, only the magnetic domains located within the exposed regions 54 will be magnetized or re-magnetized with the same polarity as the magnetic field. In addition, in some aspects the strength of the magnetic field 32 may be controlled over the length of the magnetization cycle to a value that is less than the magnitude needed to saturate the magnetic substrate 40 in the exposed regions 54. This technique can be used to control the final level of magnetization of the exposed regions 54 that can, in turn, be used to control an amount of interaction between the exposed regions 54 and a magnetic imaging medium. For example, the level of magnetization can be directly related to an ability to magnetically attract, for example, the magnetic imaging medium in the form of iron filings.

Figure 2A:
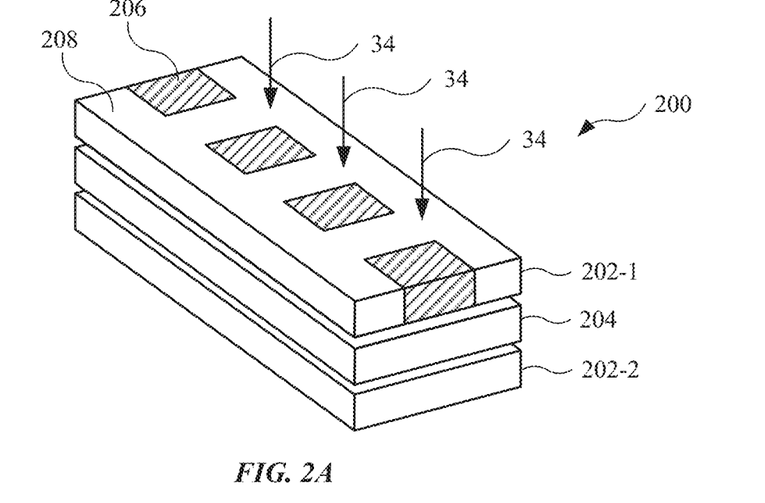
FIGS. 2A-2C shows a representative step wise process for creating a magnetic image.

FIG. 2A shows magnetic imaging assembly 200 in accordance with the described embodiments. Magnetic imaging assembly 200 can be used with magnetizer system 10 or the like for magnetically imaging a magnetic pattern on a magnetic substrate. Accordingly, magnetic imaging assembly 200 can include magnetic mask system 202 that selectively shields magnetic substrate 204 from magnetic field 32. Magnetic mask system 202 can include magnetic mask 202-1 and magnetic mask 202-2 disposed on opposite sides of magnetic substrate 204 and can include masking element 206. In the described embodiment, masking element 206 can be arranged in a pattern corresponding to a magnetic image (or its inverse). Masking element 206 can be formed of electrically conductive material (such as copper or silver) embedded in a non-electrically conductive bulk portion 208. Since masking element 206 can attenuate magnetic field 32 in accordance with a corresponding shield factor, a region of magnetic substrate 204 can be associated with a magnetic region having a corresponding level of magnetization depending in part upon an initial magnetic state of substrate 204. Accordingly the level of magnetization can be related to a magnetic image property. For example, as the level of magnetization varies, so does the ability of the corresponding magnetic region to interact with a magnetic imaging medium. In other words, a higher level of magnetization is generally associated with a correspondingly greater magnetic field strength that, in turn, can result in a higher level of interaction with the magnetic image medium.

Figure 2B:
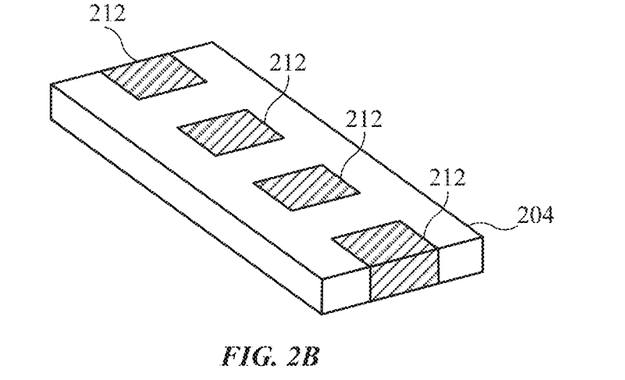

FIG. 2B shows a result of a magnetic imaging process whereby magnetic imaging assembly 200 is exposed to magnetic field 32. Accordingly, magnetic masking element 206 can attenuate to varying degrees (from little or no shielding to substantially completely blocking) magnetic field 32. In this way, the ability of magnetic field 32 to affect magnetic properties of magnetic substrate 204 can be altered. For example, a high shielding factor can essentially block magnetic field 32 leaving magnetic substrate essentially unchanged. In other cases, magnetic masking element 206 can have little ability to attenuate magnetic field 32 resulting in a potential for a substantial change in magnetic properties of magnetic substrate 204. Accordingly, regions 212 (that can be referred to as magnetic pixels or as a magnetic stencil depending upon a particular imaging technique used) can be formed in magnetic substrate 204. In this particular example, regions 212 of substrate 204 shielded by masking element 206 can retain the pre-exposure magnetic properties of magnetic substrate 204 whereas regions not shielded can have their respective magnetic properties altered by the effects of magnetic field 32. For example, if magnetic substrate 204 has a pre-magnetization polarity of P1 (opposite to that of magnetic field 32), then magnetic field 32 can alter those portions of substrate 204 not shielded by masking elements 206 by either reducing the level of magnetization of the exposed regions, neutralize the magnetic polarity of the exposed regions, or reverse the polarity of the exposed regions, all based upon the magnetic properties of substrate 204 and magnetic field 32. In this particular example, magnetic regions of substrate 204 exposed to magnetic field 32 can be effectively neutralized thereby rendering those regions essentially magnetically neutral.

Figure 2C:
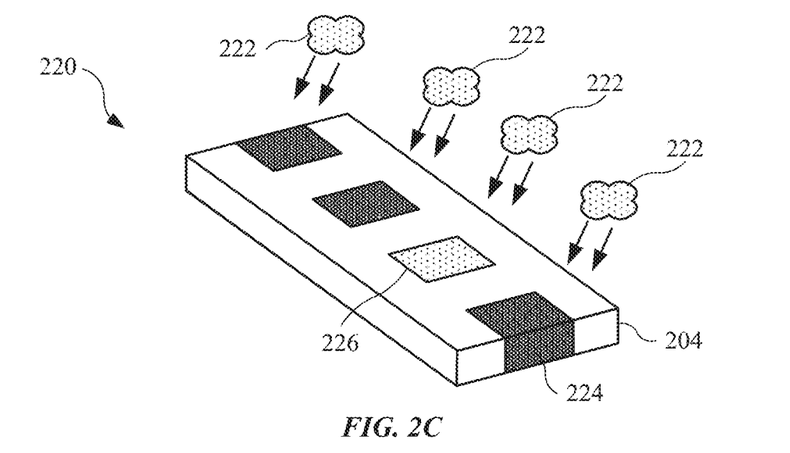

FIG. 2C shows magnetic image 220 in accordance with the described embodiments. Magnetic image 220 can be formed by exposing magnetized magnetic substrate 204 having magnetized regions 212 to a magnetic imaging medium. In general, the magnetic imaging medium can be formed of magnetically active material capable of magnetically interacting with magnetized magnetic substrate 204 in many ways. For example, the magnetic imaging medium can take the form of magnetically active particles having a relatively high mobility (such as iron filings). In another example, the magnetic imaging medium can interact with magnetized regions 212 in accordance with a magneto-optical phenomenon such as the Faraday effect in which the magnetic field from magnetized regions 212 magnetically interact with incident light by rotating the plane of polarization of the light. It should be noted that the range of rotation of the plane of polarization is linearly proportional to the component of the magnetic field in the direction of the propagation of the light. Similar to the Faraday effect where the plane of polarization of the transmitted light is rotated, the magneto-optic Kerr effect is a physical phenomenon related to light being reflected from a magnetized material, and as a result of the reflection, incurs a slightly rotated plane of polarization. However, for simplicity and without loss of generality, the magnetic imaging medium in the following examples will be considered to take the form of magnetic particles that in some cases, can be embedded in a substrate in the form of magnetic paper or more simply as mobile magnetic particles such as iron filings and the like.

The magnetic imaging medium can magnetically interact with magnetic regions 212 forming visible image 220. In the example show in FIG. 2C, an amount of magnetic imaging medium 222 has accumulated at magnetized region 212 having an effect of "developing" magnetic pixel 224 where the amount of magnetic imaging medium 222 associated with magnetic pixel 224 can be considered an image property along the lines a luminance value. For example, if magnetic imaging medium 222 takes the form of iron filings (that are generally dark grey to black in nature), then the greater the amount of iron filings attracted to magnetic region 212 can affect the image properties of magnetic pixel 224. For example, due to the inherent grey/black color of iron filings, the greater the amount of iron files attracted to magnetic region 212 (due to a higher level of magnetization) will imbue magnetic pixel 224 with a darker appearance. If, on the other hand, adjacent magnetic pixel 226 is associated with a reduced level of magnetization, then less of magnetic imaging medium will accumulate at magnetic pixel 226 giving it a less dark appearance. It is possible, therefore, to vary magnetic properties (such as a level of magnetization) of the various magnetic regions that make up magnetic image 220. In this way, the range corresponding image properties of visible image 220 can also vary. For example, magnetic pixels 224 and 226 can provide a high contrast ratio due to the disparity in levels of magnetization and corresponding interactions with the magnetic imaging medium.

Figure 3A:
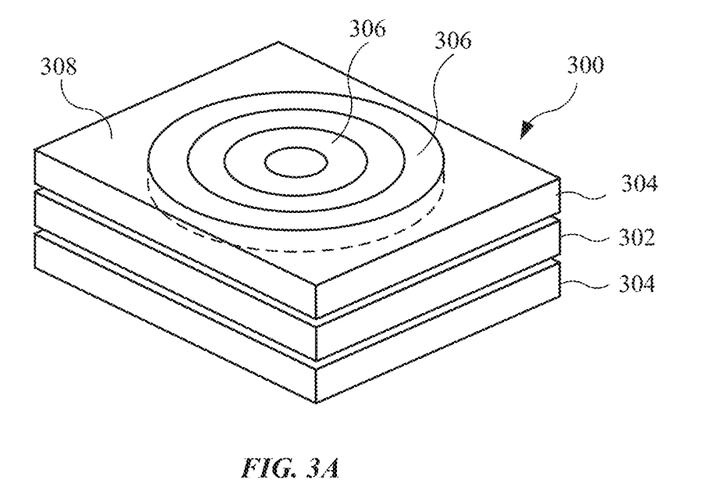
FIGS. 3A-3D illustrate various exemplary embodiments of magnetic imaging masks.
Figure 3B:
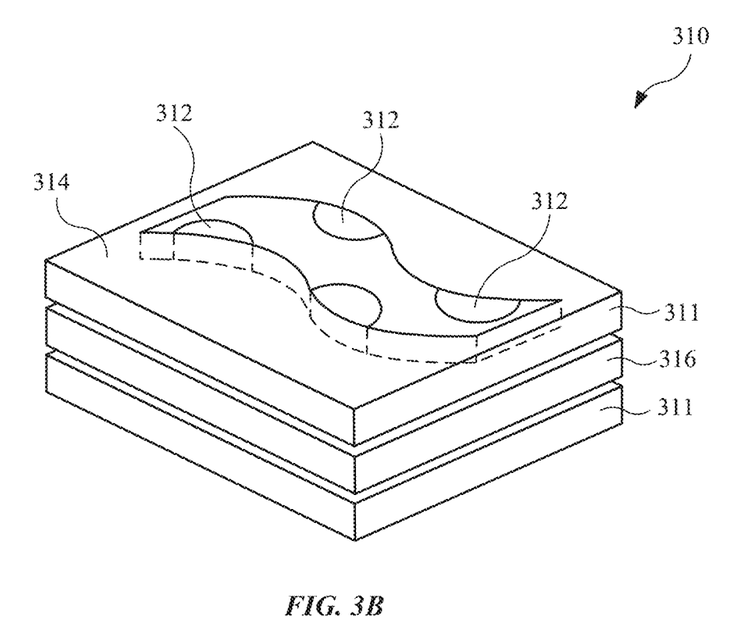

It should be noted that the system and method described herein could be used to magnetize a wide variety of magnetic substrates with different arrangements for creating a variety of magnetic images. For example, shown in FIG. 3A, magnetic imaging assembly 300 can include substrate 302 positioned between magnetic mask 304 having circular mask elements 306 that are concentrically arranged with respect to each other supported by bulk 308. In this arrangement, circular mask elements 306 can be formed of electrically conductive material having varying shielding factors. In this way, the resulting magnetic image can have circular concentric regions having different magnetic properties. Moreover, as shown in FIG. 3B, magnetic imaging assembly 310 can include mask 311 having a variety of shaped magnetized regions 312 within bulk 314 that can be used with substrate 316 that can also have a customized, non-rectilinear shape prior to the magnetization steps that form the magnetic regions. This can result in a curved multi-pole magnet that can be economically produced for inclusion within other curved structures and to perform a variety of applications. In one aspect, the magnet body, the shield bodies of the magnetic imager, and the magnetic field can be optimized to produce magnetized regions or magnetized features in the magnet body having a radius of curvature great than or about 1 millimeter.

Figure 3C:
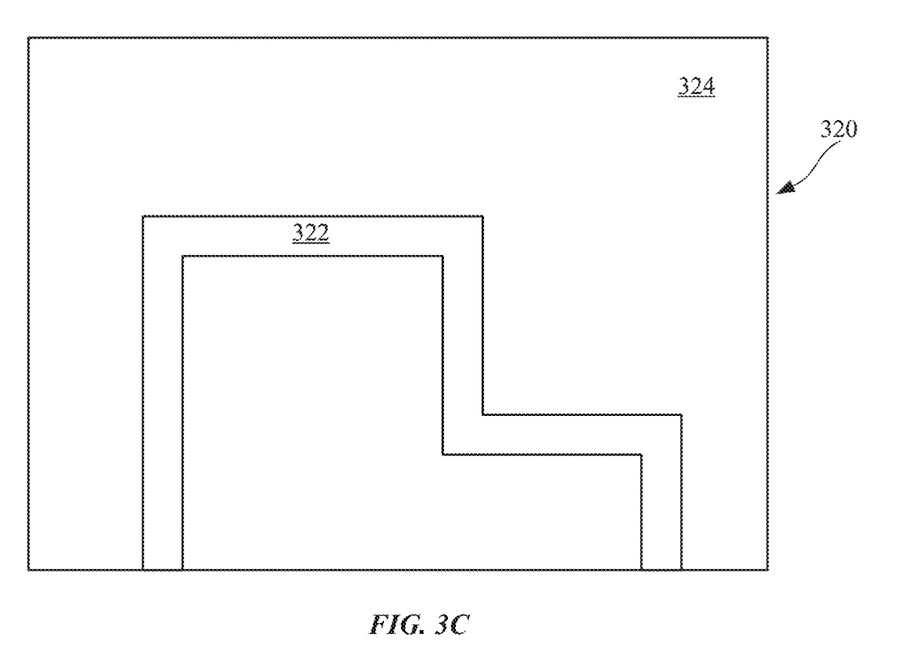
Figure 3D:
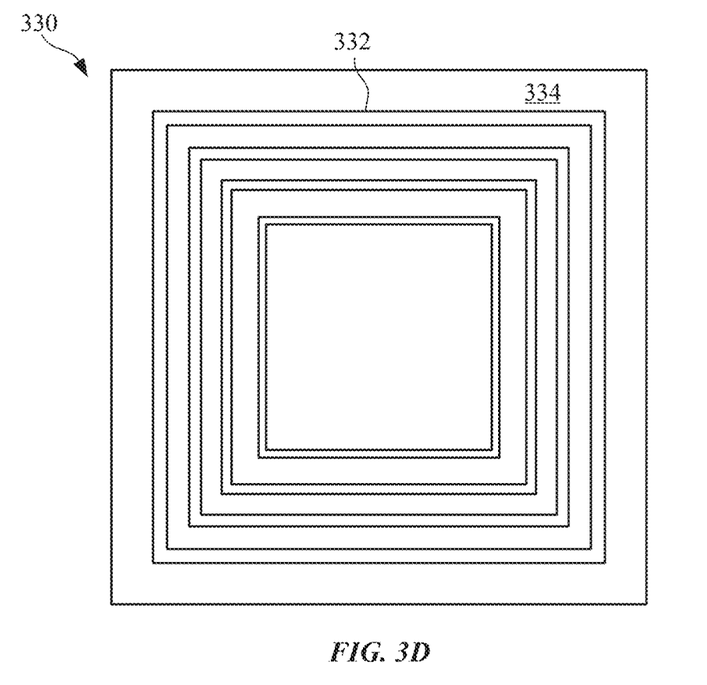

FIGS. 3C and 3D shows various rendering of magnetic masks in accordance with other described embodiments. It should be noted that magnetic mask 320, in general, includes electrically conductive regions suitable for forming eddy currents when exposed to a magnetizing magnetic field. The eddy currents, in turn, generate an opposing magnetic field that acts to attenuate the magnetizing magnetic field. The attenuation (or shield factor) can correspond to a number of properties of the electrically conductive elements, most importantly being those properties the affect the creating of eddy currents and a magnitude of the eddy currents. In addition to the amount of electrically conductive material, a ratio of the amount of electrically conductive material to non-conductive material can also affect the ability to create a magnetic image due. For example, FIG. 3C shows serpentine magnetic element 322 formed of conductive material such as copper that winds its way within substrate 324 whereas FIG. 3D shows another configuration, where magnetic mask 330 includes conductive material 332 formed into concentric rectangles surrounded by non-magnetic substrate 334.

Figure 4:
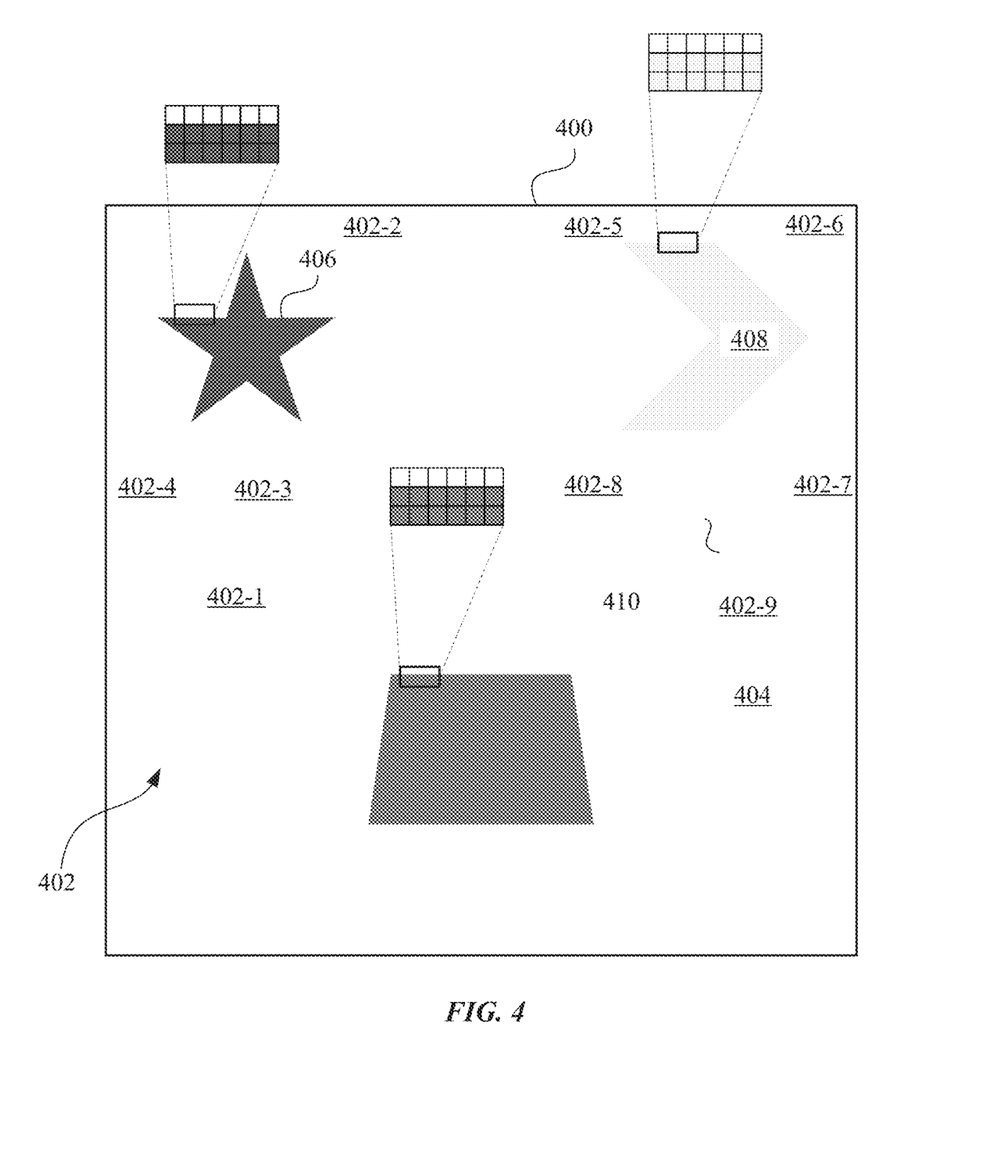
FIG. 4 shows a representative magnetic image in accordance with the described embodiments.

FIG. 4 shows representative magnetic images on magnetic substrate 400 in accordance with various techniques that can be used in accordance with the described embodiments. It should be noted that in this example, magnetic substrate 400 is considered to have a relatively low level of magnetization (or even null) compared to the levels of magnetization associated with the magnetic regions associated with the images. In this way, magnetic substrate 400 can act as a background that can help bring out the images and make them more clear and obvious. For example, image 402 can be formed of a single magnetic region 404 along the lines of a stencil. In this embodiment, the corresponding magnetic mask would essentially take on the entire shape of image 402 (as noted in the expanded region 406). In this case, the magnetic property of magnetic region 404 would exhibit generally constant magnetic properties in order to provide the seamless appearance of image 402. Image 408, on the other hand, can be produced using a collection of magnetic image elements (referred to as magnetic pixels) corresponding to individual magnetic regions that taken together can be visualized as image 408. For example, expanded region 410 highlights individual magnetic image elements 412 corresponding to magnetized regions that have magnetic properties corresponding to a corresponding portion of image 408. As can be seen, image elements 412 can have a level of magnetization that is substantially less than that of magnetic region 404 (as evidenced by the overall lighter appearance) whereas magnetic substrate 400 as above can have a level of magnetization even further reduced over that of image elements 412 providing good contrast between image 408 and magnetic substrate 400. Magnetic image 414 highlights a technique whereby both a magnetic stencil and a magnetized region corresponding to a magnetic pixel approach can be used. In particular, magnetic region 416 can have a portion 418 that exhibits substantially different magnetic properties than portion of magnetic region 416 that surrounds magnetic region 418. In this scenario, and as shown in expanded region 420, magnetic region 418 can be associated with individual magnetic regions 422 in the form of magnetic pixels whereas magnetic region 416 can be formed using the stencil technique as in image 402.

Figure 5A:
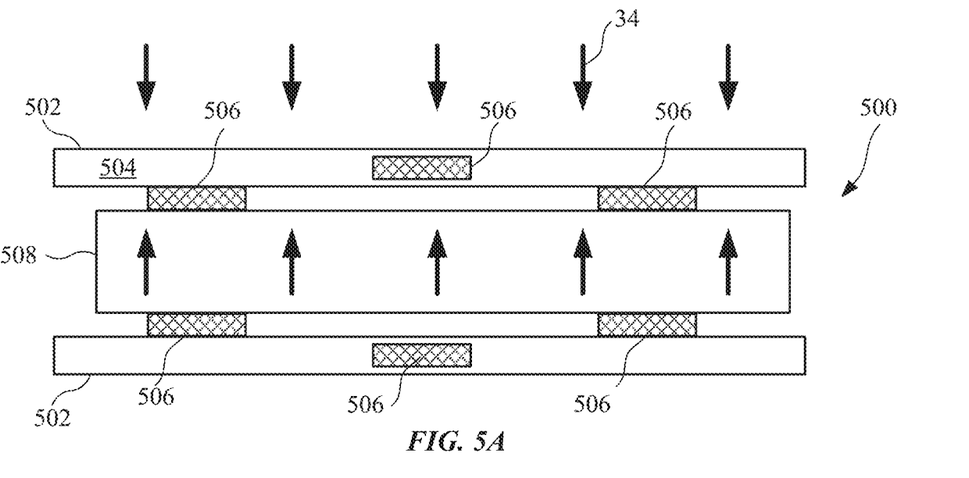
FIGS. 5A-5C shows a representative step wise process for creating a magnetic image based upon printed circuit board (PCB) technology.

In another embodiment shown in FIG. 5A, magnetic imaging assembly 500 can include magnetic mask 502 that can be fabricated using printed circuit board (PCB) technology. For example, mask 502 can include non-magnetic PCB substrate 504 and electrically conductive element 506 that can take the form of electrical traces or patterns formed in PCB substrate 504. Accordingly, magnetic mask 502 can have electrical traces patterned into PCB substrate 504 using conventional PCB technology. In this way, the electrical traces that can act as magnetic shields arranged in a pattern associated with the magnetic image. For example, as shown in FIG. 5A, magnetic imaging assembly 500 can include magnetic substrate 508 located between masks 502 where mask elements 506 shield corresponding portions of substrate 508 from magnetic field 32 creating a region corresponding to a magnetic image element. It should be noted that the actual location and properties of the magnetic image element could depend on factors such as the magnetic property of substrate 508, the shielding factors of the masking element 506, and relative strength and polarity of the magnetic field 32.

Figure 5B:
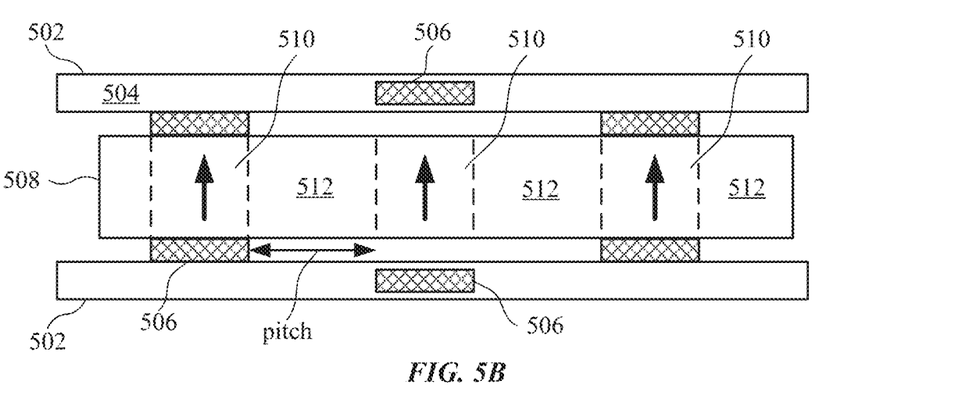
Figure 5C:
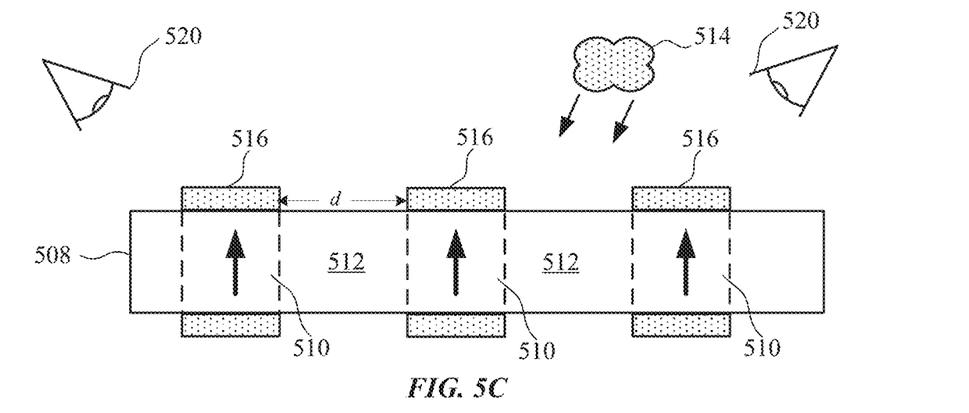

Assuming for the moment that magnetic substrate 508 has an initial polarity P1 that is opposite to that of magnetic field 32 (i.e., P2). Accordingly, when magnetic imaging assembly 500 is exposed to magnetic field 32, mask element 506 will attenuate magnetic field 32 in accordance with a corresponding shield factor. As shown in FIG. 5B, regions 510 in substrate 508 retain the original magnetic property of substrate 508 (i.e., at least polarity P1) whereas regions 512 exposed to magnetic field 32 will be affected by magnetic field 32. In this case, if the properties of substrate 508 and magnetic field 32 are balanced, then regions 512 can be effectively de-magnetized in that an overall magnetic field can be close to null. In this way, as shown in FIG. 5C, during a developing process, magnetic imaging medium 514 can magnetically interact with region 510 creating visible magnetic image element 516 separated from each other by region 512 having little or none of magnetic imaging medium 514. It should be noted that an image resolution could be associated with a distance (also referred to a pitch) between adjacent magnetic image elements. The pitch can therefore be related to a lateral distance "d" between adjacent image elements associated with region 512.

Figure 6A:
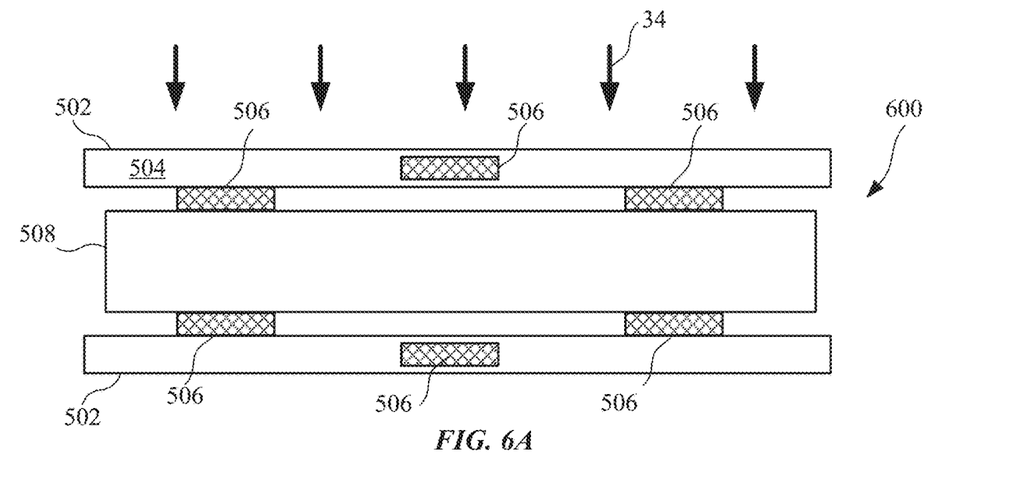
FIGS. 6A-6C illustrate the effect of the magnetic properties of the substrate can have on the magnetic image created.
Figure 6B:
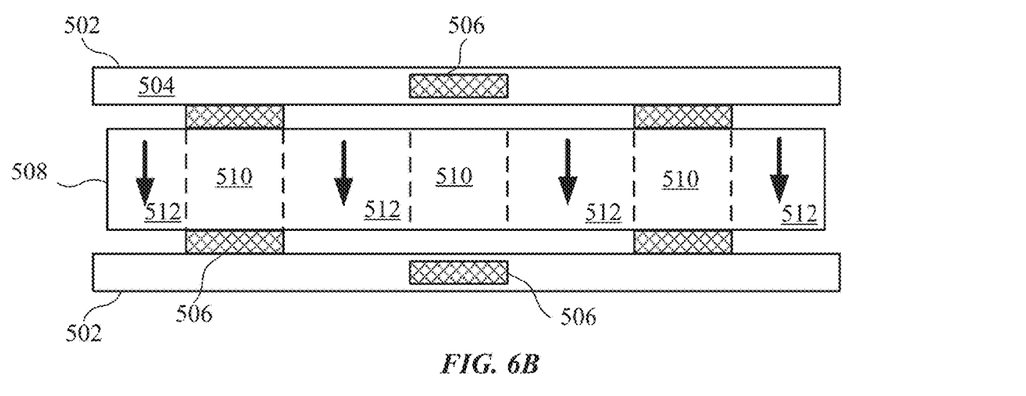
Figure 6C:
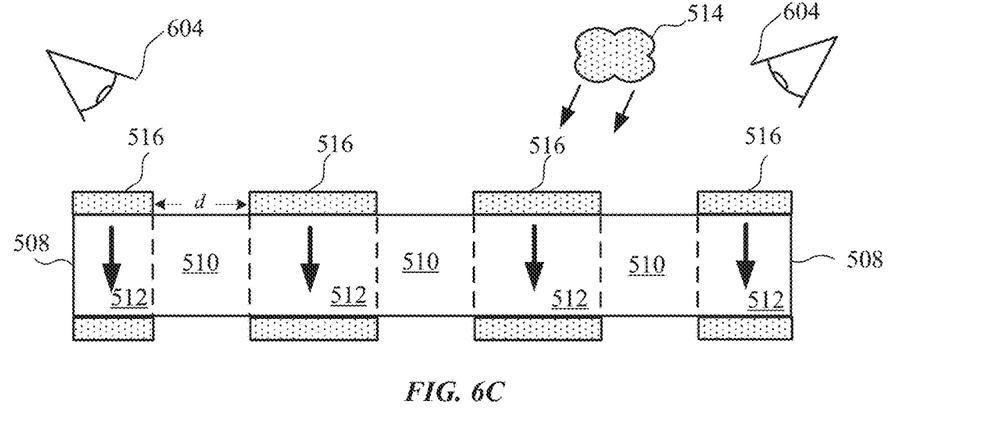

FIGS. 6A-6C illustrate the effect of the magnetic properties of the substrate can have on the magnetic image created. Accordingly, FIG. 6A shows magnetic imaging assembly 600 in accordance with the described embodiment. It should be noted that the only difference between magnetic imaging assembly 600 and magnetic imaging assembly 500 is that substrate 508 is initially un-magnetized. In this situation, masking elements 506 attenuate magnetic field 32 so that regions 512 are magnetized whereas regions 510 remain un-magnetized. In this case, image 604 is a negative version of image 520 and having a pixel pitch of d*.

Figure 7:
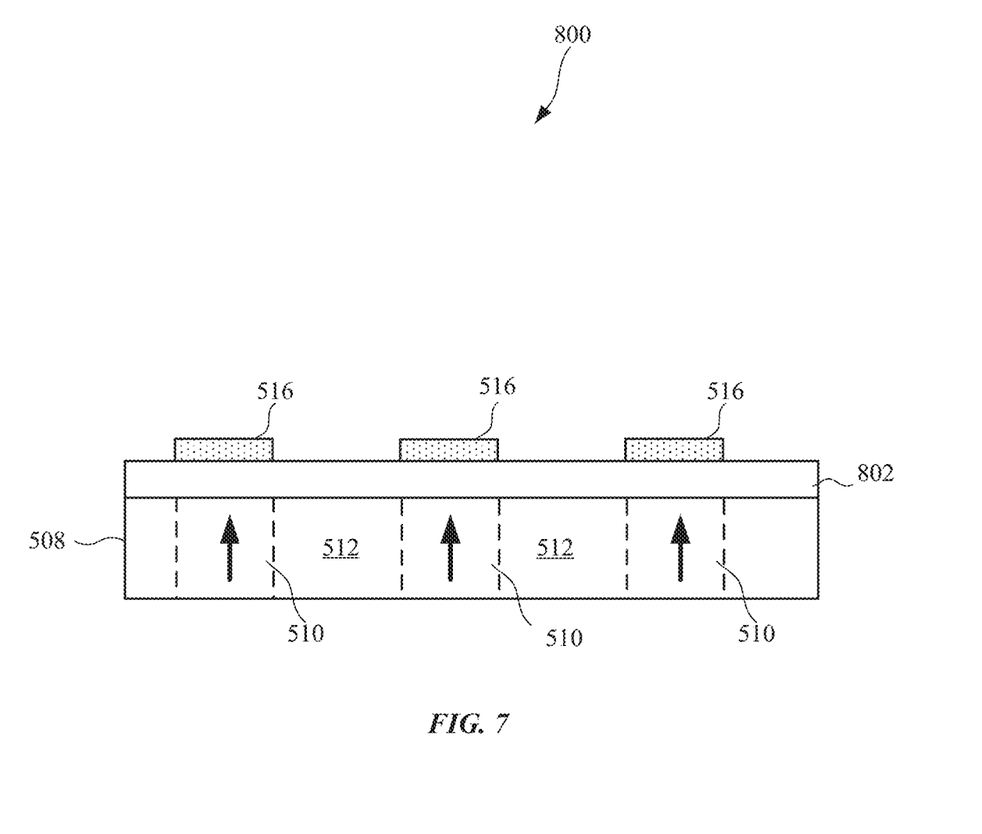
FIG. 7 shows an implementation of magnetized magnetic substrate with a magnetic image in accordance with the described embodiments.

Magnetic imaging as described herein has many uses. For example, since a magnetic image is not visible to the naked eye unless and until a magnetic imaging medium is used to develop or visualize the heretofore not visible magnetic image, information can be encoded into a magnetic substrate that can be kept secure. The secure information can then be unsecured, or viewed, simply by allowing the magnetic imaging medium to interact with the magnetic image. For example, FIG. 7 shows implementation 800 of magnetized magnetic substrate 508 with regions 510 in accordance with the described embodiments. It should be noted that image 520 could take many forms such as an indicium (such as a logo or trademark), an alphanumeric code indicative of, for example, part identification, and so on. In the embodiment shown, magnetized substrate 508 can be overlaid with non-magnetic substrate 802. In this way, magnetic field lines 804 emanating from regions 510 can penetrate to exterior surface 806 of non-magnetic substrate 802 forming magnetic surface 808 corresponding to image 520 that can be formed of magnetic pixels 516. In this way, an interaction between magnetic imaging medium and magnetic surface 808 can visualize image 520.

Figure 8A:
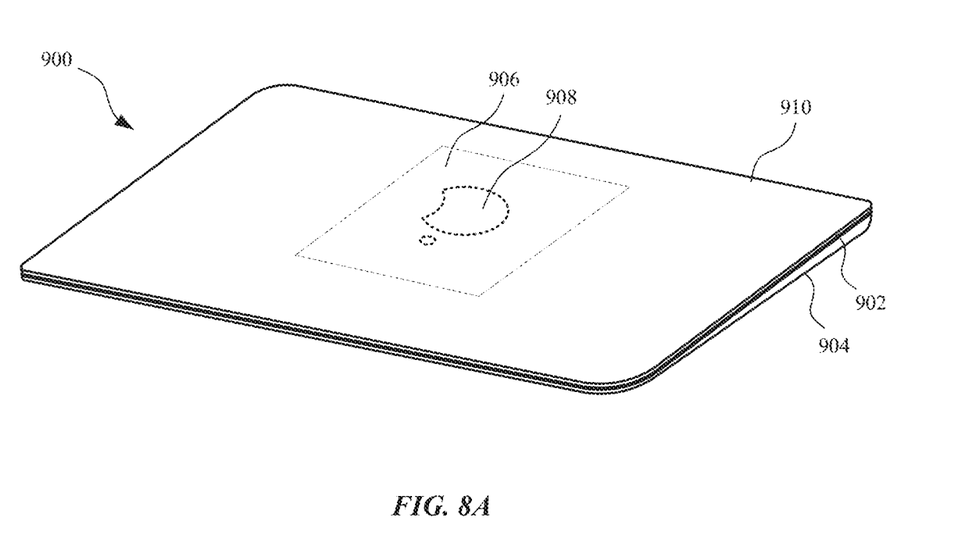
FIGS. 8A and 8B illustrate a particularly useful application of magnetic imaging in accordance with the described embodiments.
Figure 8B:
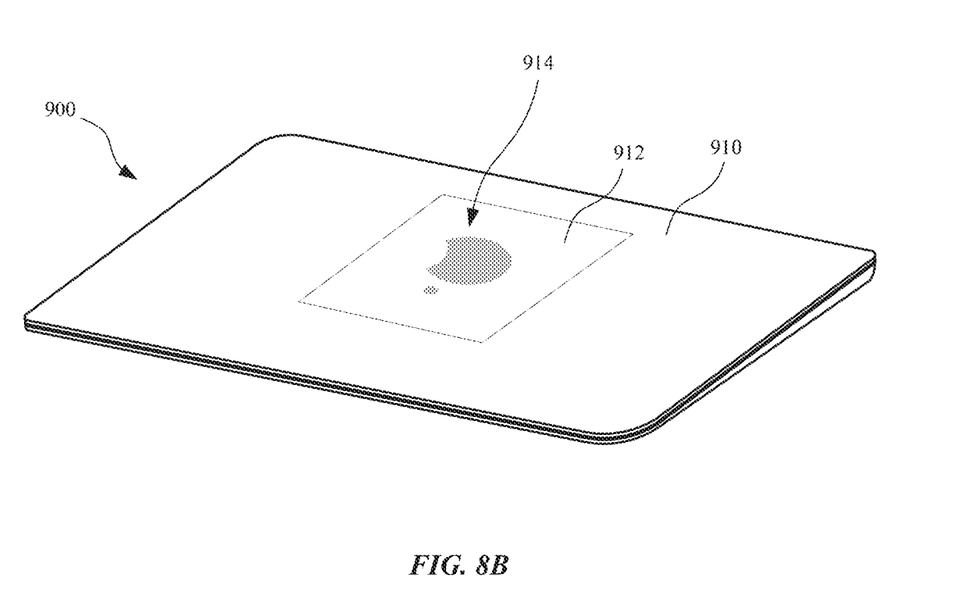

Accordingly, FIGS. 8A and 8B illustrate a particularly useful application of magnetic imaging in accordance with the described embodiments. FIG. 8A shows electronic device 900 in accordance with the described embodiments (in this case, electronic device 900 can take the form of a laptop computer). Electronic device 900 can include lid 902 pivotally coupled to base unit 904 which in a closed configuration as shown, has an appearance of a single piece. It should be noted that in this example at least lid 902 can be formed of a non-magnetic material, such as plastic, non-magnetic metal such as aluminum, and so on. Moreover, lid 902 includes magnetic substrate 906 having a magnetic image magnetically encoded therein. It should be noted that the dotted lines indicate that magnetic substrate 906 and the magnetic image are not visible through lid 902. However, due to the non-magnetic nature of lid 902, magnetic field lines emanating from magnetic pixels associated with the magnetic image penetrate lid 902 form magnetic surface 908 on exterior surface 910 that is a direct analog of the magnetic image encoded into magnetic substrate 906. Accordingly, magnetic imaging medium can be used to visualize the magnetic image by allowing the magnetic imaging medium to magnetically interact with magnetic surface 908. It should also be noted, that due to the non-magnetic nature of lid 902, magnetic image 908 can be modified by simply applying a magnetizing magnetic field to lid 902 of sufficient strength, duration, and polarity to modify the regions in magnetic substrate 906 corresponding to magnetic pixels. In another embodiment, at least lid 902 (or a portion thereof) can be formed of magnetic material. In this way, a portion of lid 902 can be magnetized to form magnetic surface 908 using magnetic imaging system 10.

FIG. 8B shows a particular manner in visualizing the magnetic image encoded into magnetic substrate 906 using magnetic imaging medium 912 placed in proximity or in contact with exterior surface 910. In this case, magnetic imaging medium 912 takes the form of magnetic paper in which magnetic particles are embedded in a sheet formed of non-magnetic material such as plastic. In this case, the magnetic particles will be attracted to the magnetic surface 908 and collectively provide a representation of magnetic image 914 that can now be easily seen due to the collective interaction between magnetic surface 908 and the magnetic particles embedded within magnetic imaging medium 912.

Figure 9:
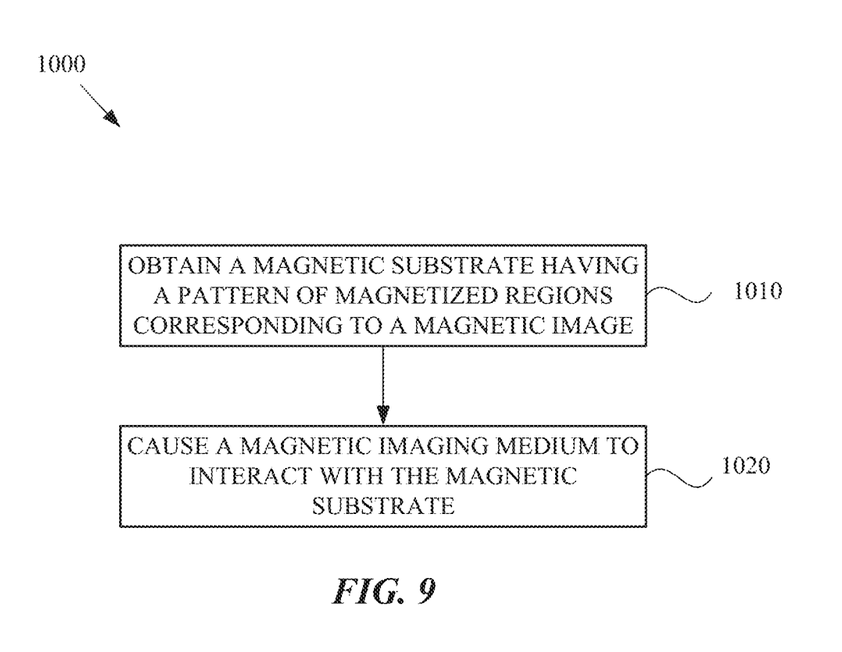
FIG. 9 shows a flowchart detailing a process in accordance with the described embodiments.

FIG. 9 shows a flowchart detailing process 1000 in accordance with the described embodiments. Process 1000 can be used for rendering magnetic regions on a magnetic substrate visible. In one embodiment, the magnetic regions can collectively form a magnetic image. Accordingly, process 1000 can begin at 1010 by obtaining a magnetic substrate having a pattern of magnetized regions corresponding to a magnetic image. Next at 1020, a magnetic imaging medium can be caused to interact with the magnetic regions. In one embodiment, the magnetic imaging medium can take the form of mobile magnetic particles along the lines of iron filings or other magnetic particles. The mobile magnetic medium will interact with the magnetic regions in accordance with a magnetic property of the magnetic regions. For example, an amount of the mobile magnetic medium that interacts with the magnetic region can be associated with a magnetic property such as a level of magnetic saturation. Accordingly, a visible variation in the amount or kind of magnetic particles can be perceived as a gradation in "color" (if the mobile particles have an inherent color) or as a grey scale image if the mobile magnetic particles are a mix of mobile magnetic particles (i.e., some particles may be white, some black, some grey each with a different propensity to interact with a magnetic region thereby providing a variation in visible content in the magnetic image). The various aspects, embodiments, implementations or features of the described embodiments can be used separately or in any combination.

Various aspects of the described embodiments can be implemented by software, hardware or a combination of hardware and software. The described embodiments can also be embodied as computer readable code on a computer readable medium. The computer readable medium is any data storage device that can store data that can thereafter be read by a computer system. Examples of the computer readable medium include read-only memory, random-access memory, CD-ROMs, DVDs, magnetic tape, hard disk drives, solid state drives, and optical data storage devices. The computer readable medium can also be distributed over network-coupled computer systems so that the computer readable code is stored and executed in a distributed fashion.

The foregoing description, for purposes of explanation, uses specific nomenclature to provide a thorough understanding of the described embodiments. However, it will be apparent to one skilled in the art that the specific details are not required in order to practice the described embodiments. Thus, the foregoing descriptions of specific embodiments are presented for purposes of illustration and description. They are not intended to be exhaustive or to limit the described embodiments to the precise forms disclosed. It will be apparent to one of ordinary skill in the art that many modifications and variations are possible in view of the above teachings.

What is claimed is:

1. A method for forming a magnetic image on a magnetic substrate, comprising:
   positioning a magnetic imaging mask between a magnetizer and the magnetic substrate, wherein the magnetic imaging mask includes magnetic shields capable of magnetically shielding masked regions of the magnetic substrate that are overlaid by the magnetic shields from a magnetizing magnetic field, wherein the masked regions are separated by exposed regions of the magnetic substrate;
   directing, by the magnetizer, the magnetizing magnetic field at the magnetic substrate such as to form a pattern of magnetized regions on the magnetic substrate, wherein the pattern of magnetized regions corresponds to the exposed regions; and
   forming the magnetic image on the magnetic substrate by using a magnetic imaging medium to magnetically interact with the pattern of magnetizable regions.

2. The method as recited in claim 1, wherein the magnetic imaging medium magnetically interacts with the pattern of magnetized regions in accordance with a level of magnetization up to and including a saturation level associated with the magnetic substrate.

3. The method as recited in claim 1, wherein the magnetic shields include conductive material that causes a formation of eddy currents in response to the magnetizing magnetic field passing through the magnetic imaging mask.

4. The method as recited in claim 1, wherein the magnetic imaging medium includes magnetic particles that are capable of interacting with the pattern of magnetized regions.

5. The method as recited in claim 1, wherein the magnetic imaging mask includes a printed circuit board having at least one electrical trace corresponding to the magnetic shields.

6. The method as recited in claim 1, wherein the magnetic image includes at least one of a bar code, a QR code, an indicium or a magnetic ink identification number.

7. The method as recited in claim 1, wherein the magnetic image is rendered visible and characterized as having a gray-scale image.

8. A portable electronic device, comprising:
   a housing including a magnetizable substrate, the magnetizable substrate including a first magnetic region having a first level of magnetization, a second magnetic region having a second level of magnetization, wherein each of the first level of magnetization and second level of magnetization corresponds to a respective magnetically encoded luminance value.

9. The portable electronic device as recited in claim 8, further comprising an un-magnetized region disposed between the first and second magnetic regions.

10. The portable electronic device as recited in claim 9, wherein the un-magnetized region corresponds to a null magnetic pixel having a null luminance value.

11. The portable electronic device as recited in claim 8, wherein the first magnetic region corresponds to a first magnetic pixel having a first luminance value and the second magnetic region corresponds to a second magnetic pixel having a second luminance value.

12. The portable electronic device as recited in claim 8, wherein each of the magnetically encoded luminance values corresponds to a respective gray-scale luminance value such that the first and second magnetic regions together form a gray-scale visual image.

13. The portable electronic device as recited in claim 8, wherein the magnetically encoded luminance information corresponds to a bar code, a QR code, an indicium, or a magnetic ink identification number.

14. A magnetic imaging system for forming a magnetic image on a magnetic substrate, the magnetic imaging system comprising:
   a magnetizer arranged to generate a magnetizing magnetic field at the magnetic substrate such as to form a pattern of magnetized regions on the magnetic substrate;
   a magnetic imaging mask including magnetic shields that are arranged in a pattern corresponding to the magnetic image;
   a magnetic fixturing device capable of positioning the magnetic substrate relative to the magnetizer and the magnetic imaging mask such that the magnetic shields are capable of shielding masked regions of the magnetic substrate that are overlaid by the magnetic shields from the magnetizing magnetic field, wherein the masked regions are separated by exposed regions of the magnetic substrate; and
   a magnetic imaging medium arranged to magnetically interact with the pattern of magnetized regions to form the magnetic image, wherein the pattern of magnetized regions corresponds to the exposed regions.

15. The magnetic imaging system as recited in claim 14, wherein the magnetic shields comprise a shielding factor corresponding to a magnetic property of the magnetic image.

16. The magnetic imaging system as recited in claim 15, wherein the magnetic property comprises a level of magnetization.

17. The magnetic imaging system as recited in claim 16, wherein the level of magnetization corresponds to luminance.

18. The magnetic imaging system as recited in claim 17, wherein the luminance corresponds to a degree of interaction between the exposed regions and the magnetic imaging medium.

19. The magnetic imaging system as recited in claim 14, wherein the magnetic imaging medium includes magnetic particles that are capable of interacting with the pattern of magnetized regions.

20. The magnetic imaging system as recited in claim 14, wherein the magnetic shields include conductive material that causes a formation of eddy currents in response to the magnetizing magnetic field passing through the magnetic imaging mask.

* * * * *